US008575307B2

(12) United States Patent
Shafrir et al.

(10) Patent No.: US 8,575,307 B2
(45) Date of Patent: Nov. 5, 2013

(54) PROTEIN KINASE C INHIBITORS FOR PREVENTION OF INSULIN RESISTANCE AND TYPE 2 DIABETES

(75) Inventors: Eleazar Shafrir, Jerusalem (IL); Ehud Ziv, Moza Ilit (IL); Hadas Reuveni, Har-adar (IL); Masha Niv, Beit Zayit (IL)

(73) Assignee: Hadasit Medical Research Services & Development Ltd., Jerusalem (IL)

( * ) Notice: Subject to any disclaimer, the term of this patent is extended or adjusted under 35 U.S.C. 154(b) by 933 days.

(21) Appl. No.: 11/993,691

(22) PCT Filed: Jun. 28, 2006

(86) PCT No.: PCT/IL2006/000755
§ 371 (c)(1),
(2), (4) Date: May 10, 2010

(87) PCT Pub. No.: WO2007/000770
PCT Pub. Date: Jan. 4, 2007

(65) Prior Publication Data
US 2010/0216701 A1 Aug. 26, 2010

Related U.S. Application Data

(60) Provisional application No. 60/694,691, filed on Jun. 29, 2005.

(51) Int. Cl.
| *A61K 38/04* | (2006.01) |
| *A61K 38/00* | (2006.01) |
| *A61K 38/28* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 2/00* | (2006.01) |
| *C07K 4/00* | (2006.01) |
| *C07K 14/00* | (2006.01) |
| *A61P 3/08* | (2006.01) |
| *A61P 3/10* | (2006.01) |
| *A61P 5/50* | (2006.01) |
| *A61P 7/12* | (2006.01) |

(52) U.S. Cl.
USPC ............ 530/327; 530/300; 530/333; 514/6.8; 514/6.7; 514/7.3; 514/1.1

(58) Field of Classification Search
None
See application file for complete search history.

(56) References Cited

U.S. PATENT DOCUMENTS

| 4,923,802 | A | * | 5/1990 | Gallis | 435/15 |
| 5,783,405 | A | | 7/1998 | Mochly-Rosen et al. | |
| 6,306,383 | B1 | * | 10/2001 | Crandall | 424/78.06 |
| 6,511,811 | B1 | * | 1/2003 | Olefsky et al. | 435/7.1 |
| 6,686,334 | B2 | | 2/2004 | Messing et al. | |
| 6,811,993 | B2 | * | 11/2004 | King | 435/15 |
| 6,881,334 | B2 | * | 4/2005 | Janik | 210/232 |
| 7,892,730 | B2 | * | 2/2011 | Morris et al. | 435/6.16 |
| 2002/0182586 | A1 | * | 12/2002 | Morris et al. | 435/4 |

FOREIGN PATENT DOCUMENTS

| JP | 2002-500649 A | 1/2002 |
| JP | 2002-504899 A | 2/2002 |
| JP | 2002-525382 A | 8/2002 |
| WO | 98/53050 A2 | 11/1998 |
| WO | 98/53051 A1 | 11/1998 |
| WO | 00/01415 A2 | 1/2000 |
| WO | 00/01805 A1 | 1/2000 |
| WO | 00/18895 A1 | 4/2000 |
| WO | 2005/025602 A1 | 3/2005 |

OTHER PUBLICATIONS

U. Kikkawa et al., "The protein kinase C family: heterogeneity and its implications," Annu. Rev. Biochem., 1989, vol. 58; pp. 31-44.
D. Knighton et al., "Structure of a peptide inhibitor bound to the catalytic subunit of cyclic adenosine monophosphate-dependent protein kinase," Science, 1991, vol. 253, pp. 414-420.
Anis et al.: "Antidiabetic effect of novel modulating peptides of G-protein-coupled kinase in experimental models of diabetes," Diabetologia, 2004, vol. 47; pp. 1232-1244.
Borek et al.: "Long-chain (sphingoid) bases inhibit multistage carcinogenesis in mouse C3H/10T1/2 cells treated with radiation and phorbol 12-myristate 13-acetate," Proc. Natl. Acad. Sci. USA, 1991, vol. 88; pp. 1953-1957.
Maegawa et al.: "Impaired autophosphorylation of insulin receptors from abdominal skeletal muscles in nonobese subjects with NIDDM," Diabetes, 1991, vol. 40; pp. 815-819.
Kikkawa et al.: "The protein kinase C family: heterogeneity and its implications," Annu. Rev. Biochem., 1989, vol. 58; pp. 31-44.
Nishizuka: "Intracellular signaling by hydrolysis of phospholipids and activation of protein kinase C," Science, 1992, vol. 258; pp. 607-614.
Niv et al.: "Sequence-based Design of Kinase Inhibitors Applicable for Therapeutics and Target Identification," J. Biol. Chem., 2004, vol. 279, No. 2; pp. 1242-1255.
Nolan et al.: "Role of human skeletal muscle insulin receptor kinase in the in vivo insulin resistance of noninsulin-dependent diabetes mellitus and obesity," J. Clin. Endocrinol. Metab., 1994, vol. 78, No. 2; pp. 471-477.
Knighton et al.: "Structure of a peptide inhibitor bound to the catalytic subunit of cyclic adenosine monophosphate-dependent protein kinase," Science, 1991, vol. 253; pp. 414-420.
Schaap D. et al.: "Unique substrate specificity and regulatory properties of PKC-ε: a rationale for diversity," FEBS Letters, 1989, vol. 243, No. 2; pp. 351-357.

* cited by examiner

*Primary Examiner* — Maury Audet
(74) *Attorney, Agent, or Firm* — Rothwell, Figg, Ernst & Manbeck, P.C.

(57) ABSTRACT

The present invention provides peptides and peptide analogs capable of inhibiting the activity of protein kinase C. The invention discloses use of such peptides and analogs for preparation of pharmaceutical compositions and methods for prevention, delay, suppression or treatment of type 2 diabetes using such compositions.

5 Claims, 8 Drawing Sheets

SEQUENCE LISTING

```
<160> NUMBER OF SEQ ID NOS: 9

<210> SEQ ID NO 1
<211> LENGTH: 737
<212> TYPE: PRT
<213> ORGANISM: Homo sapiens

<400> SEQUENCE: 1

Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
    50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
```

```
                100             105             110
Phe Glu Asp Trp Ile Asp Leu Glu Pro Glu Gly Arg Val Tyr Val Ile
            115                 120             125
Ile Asp Leu Ser Gly Ser Ser Gly Glu Ala Pro Lys Asp Asn Glu Glu
            130                 135             140
Arg Val Phe Arg Glu Arg Met Arg Pro Arg Lys Arg Gln Gly Ala Val
145             150                 155                 160
Arg Arg Arg Val His Gln Val Asn Gly His Lys Phe Met Ala Thr Tyr
                165                 170             175
Leu Arg Gln Pro Thr Tyr Cys Ser His Cys Arg Asp Phe Ile Trp Gly
            180                 185             190
Val Ile Gly Lys Gln Gly Tyr Gln Cys Gln Val Cys Thr Cys Val Val
            195                 200             205
His Lys Arg Cys His Glu Leu Ile Ile Thr Lys Cys Ala Gly Leu Lys
        210                 215             220
Lys Gln Glu Thr Pro Asp Gln Val Gly Ser Gln Arg Phe Ser Val Asn
225             230                 235                 240
Met Pro His Lys Phe Gly Ile His Asn Tyr Lys Val Pro Thr Phe Cys
            245                 250             255
Asp His Cys Gly Ser Leu Leu Trp Gly Leu Leu Arg Gln Gly Leu Gln
            260                 265             270
Cys Lys Val Cys Lys Met Asn Val His Arg Arg Cys Glu Thr Asn Val
            275                 280             285
Ala Pro Asn Cys Gly Val Asp Ala Arg Gly Ile Ala Lys Val Leu Ala
            290                 295             300
Asp Leu Gly Val Thr Pro Asp Lys Ile Thr Asn Ser Gly Gln Arg Arg
305             310                 315                 320
Lys Lys Leu Ile Ala Gly Ala Glu Ser Pro Gln Pro Ala Ser Gly Ser
                325                 330             335
Ser Pro Ser Glu Glu Asp Arg Ser Lys Ser Ala Pro Thr Ser Pro Cys
            340                 345             350
Asp Gln Glu Ile Lys Glu Leu Glu Asn Asn Ile Arg Lys Ala Leu Ser
            355                 360             365
Phe Asp Asn Arg Gly Glu Glu His Arg Ala Ala Ser Ser Pro Asp Gly
            370                 375             380
Gln Leu Met Ser Pro Gly Glu Asn Gly Glu Val Arg Gln Gly Gln Ala
385             390                 395                 400
Lys Arg Leu Gly Leu Asp Glu Phe Asn Phe Ile Lys Val Leu Gly Lys
                405                 410             415
Gly Ser Phe Gly Lys Val Met Leu Ala Glu Leu Lys Gly Lys Asp Glu
            420                 425             430
Val Tyr Ala Val Lys Val Leu Lys Lys Asp Val Ile Leu Gln Asp Asp
            435                 440             445
Asp Val Asp Cys Thr Met Thr Glu Lys Arg Ile Leu Ala Leu Ala Arg
            450                 455             460
Lys His Pro Tyr Leu Thr Gln Leu Tyr Cys Cys Phe Gln Thr Lys Asp
465             470                 475                 480
Arg Leu Phe Phe Val Met Glu Tyr Val Asn Gly Gly Asp Leu Met Phe
                485                 490             495
Gln Ile Gln Arg Ser Arg Lys Phe Asp Glu Pro Arg Ser Arg Phe Tyr
            500                 505             510
Ala Ala Glu Val Thr Ser Ala Leu Met Phe Leu His Gln His Gly Val
            515                 520             525
```

-continued

```
Ile Tyr Arg Asp Leu Lys Leu Asp Asn Ile Leu Leu Asp Ala Glu Gly
            530                 535                 540
His Cys Lys Leu Ala Asp Phe Gly Met Cys Lys Glu Gly Ile Leu Asn
545                 550                 555                 560
Gly Val Thr Thr Thr Thr Phe Cys Gly Thr Pro Asp Tyr Ile Ala Pro
                565                 570                 575
Glu Ile Leu Gln Glu Leu Glu Tyr Gly Pro Ser Val Asp Trp Trp Ala
            580                 585                 590
Leu Gly Val Leu Met Tyr Glu Met Met Ala Gly Gln Pro Pro Phe Glu
        595                 600                 605
Ala Asp Asn Glu Asp Asp Leu Phe Glu Ser Ile Leu His Asp Asp Val
    610                 615                 620
Leu Tyr Pro Val Trp Leu Ser Lys Glu Ala Val Ser Ile Leu Lys Ala
625                 630                 635                 640
Phe Met Thr Lys Asn Pro His Lys Arg Leu Gly Cys Val Ala Ser Gln
                645                 650                 655
Asn Gly Glu Asp Ala Ile Lys Gln His Pro Phe Phe Lys Glu Ile Asp
            660                 665                 670
Trp Val Leu Leu Glu Gln Lys Lys Ile Lys Pro Pro Phe Lys Pro Arg
        675                 680                 685
Ile Lys Thr Lys Arg Asp Val Asn Asn Phe Asp Gln Asp Phe Thr Arg
    690                 695                 700
Glu Glu Pro Val Leu Thr Leu Val Asp Glu Ala Ile Val Lys Gln Ile
705                 710                 715                 720
Asn Gln Glu Glu Phe Lys Gly Phe Ser Tyr Phe Gly Glu Asp Leu Met
                725                 730                 735
Pro

<210> SEQ ID NO 2
<211> LENGTH: 32
<212> TYPE: PRT
<213> ORGANISM: Homo sapiens

<400> SEQUENCE: 2

Asn Gly Gly Asp Leu Met Phe Gln Ile Gln Arg Ser Arg Lys Phe Asp
1               5                   10                  15
Glu Pro Arg Ser Arg Phe Tyr Ala Ala Glu Val Thr Ser Ala Leu Met
            20                  25                  30

<210> SEQ ID NO 3
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Any amino acid

<400> SEQUENCE: 3

Xaa Phe Gln Ile Gln Arg Ser Arg Lys Phe Asn
1               5                   10

<210> SEQ ID NO 4
<211> LENGTH: 13
<212> TYPE: PRT
<213> ORGANISM: Artificial
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa = Any amino acid

<400> SEQUENCE: 4

Xaa Asn Leu Met Phe Gln Ile Gln Arg Ser Arg Lys Phe
1               5                   10

<210> SEQ ID NO 5
<211> LENGTH: 32
<212> TYPE: PRT
<213> ORGANISM: Homo sapiens

<400> SEQUENCE: 5

Glu Met Met Ala Gly Gln Pro Pro Phe Glu Ala Asp Asn Glu Asp Asp
1               5                   10                  15

Leu Phe Glu Ser Ile Leu His Asp Asp Val Leu Tyr Pro Val Trp Leu
            20                  25                  30

<210> SEQ ID NO 6
<211> LENGTH: 11
<212> TYPE: PRT
<213> ORGANISM: Artificial
<220> FEATURE:
<223> OTHER INFORMATION: Synthetic peptide

<400> SEQUENCE: 6

Gly Phe Gln Ile Gln Arg Ser Arg Lys Phe Asn
1               5                   10

<210> SEQ ID NO 7
<211> LENGTH: 13
<212> TYPE: PRT
<213> ORGANISM: Artificial
<220> FEATURE:
<223> OTHER INFORMATION: Synthetic peptide

<400> SEQUENCE: 7

Gly Asn Leu Met Phe Gln Ile Gln Arg Ser Arg Lys Phe
1               5                   10

<210> SEQ ID NO 8
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Any amino acid

<400> SEQUENCE: 8

Xaa Met Ala Lys Gln Pro Pro Phe
1               5

<210> SEQ ID NO 9
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Xaa = Any amino acid
<220> FEATURE:
<221> NAME/KEY: MOD_RES
<222> LOCATION: (4)..(4)
```

```
<223> OTHER INFORMATION: D-Lys

<400> SEQUENCE: 9

Gly Met Ala Lys Gln Pro Pro Phe
1               5
```

PROTEIN KINASE C INHIBITORS FOR PREVENTION OF INSULIN RESISTANCE AND TYPE 2 DIABETES

This application is a 35 U.S.C. §371 National Phase of International Application Serial No. PCT/IL2006/000755, filed Jun. 28, 2006, and claims the benefit of U.S. Provisional Application No. 60/694,691 filed Jun. 29, 2005.

FIELD OF THE INVENTION

The present invention relates to therapeutic peptides, peptide analogs and peptidomimetics and to methods useful for prevention, delay, suppression or treatment of type 2 diabetes, insulin resistance and other conditions by inhibition of protein kinase C.

BACKGROUND OF THE INVENTION

Protein Kinase C

Protein kinase C, PKC, belongs to a family of widely distributed signal transduction proteins important for cell growth, differentiation, and other responses. PKC consists of a family of closely related enzymes that function as serine/threonine kinases. PKC is activated by growth factors, hormones, and other external messengers via stimulation of phospholipase C and is responsible for the generation of the second messengers inositol triphosphate and diacylglycerol.

At present, there are at least eleven known isozymes of PKC that differ in their tissue distribution, enzymatic specificity, and regulation (Nishizuka Y. Annu. Rev. Biochem. 1989, 58: 31-44; Nishizuka Y. Science 1992, 258: 607-614). PKC belongs to a group sensitive to activation by diacylglycerol (DAG). DAG is a product of increased triglycerides (TG) turnover, related to elevated tissue TG content, prominent in muscles of insulin resistant individuals. Because of the DAG sensitivity, some of the PKC isoenzymes have been termed "lipid second messengers". A specific function of each PKC isoenzyme has not been yet firmly established, however it is known that they preferentially phosphorylate serine and threonine residues. Several PKC isoenzymes, as PKCα, PKC-ε and PKCθ have been shown, both in animals and humans, to be related to insulin resistance by serine phosphorylation, which is inhibitory to tyrosine phosphorylation and to insulin signaling.

Protein kinase C isozymes are single polypeptide chains ranging from 592 to 737 amino acids in length. The isozymes contain a regulatory domain and a catalytic domain connected by a linker peptide. The regulatory and catalytic domains can be further subdivided into constant and variable regions. The catalytic domain of protein kinase C is very similar to that seen in other protein kinases while the regulatory domain is unique to the PKC isozymes. The PKC isozymes demonstrate between 40-80% homology at the amino acid level among the group. However, the homology of a single isozyme between different species is generally greater than 97%.

The protein kinase C isozymes, alpha, beta-1, beta-2 and gamma, require membrane phospholipid, calcium and diacylglycerol/phorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipid for their activation.

The ubiquitous nature of the protein kinase C isozymes and their important roles in physiology provide incentives to produce highly selective PKC inhibitors. Given the evidence demonstrating linkage of certain isozymes to disease states, it is reasonable to assume that inhibitory compounds that are selective to one or two protein kinase C isozymes relative to the other PKC isozymes and other protein kinases are superior therapeutic agents. Such compounds demonstrate greater efficacy and lower toxicity by virtue of their specificity.

Chronic activation of PKC results in abnormal cellular proliferation and tumor formation. Increased tumorigenicity is also correlated with overexpression of PKC in cultured cells inoculated into nude mice. A mutant form of PKC induces highly malignant tumor cells with increased metastatic potential. Sphingosine and related inhibitors of PKC activity have been shown to inhibit tumor cell growth and radiation-induced transformation in vivo (Borek et al., 1991, Proc. Natl. Acad. Sci., 88, 1953-1957). A number of experimental or clinically useful anti-cancer drugs show modulatory effects on PKC. Therefore, inhibitors of PKC may be important cancer-preventive or therapeutic agents.

Experiments also indicate that PKC plays an important role in the pathophysiology of hyperproliferative skin disorders such as psoriasis and skin cancer.

Diabetes

Diabetes mellitus is the most common endocrine disorder and is a chronic condition. It is estimated that in 1999 there were 100 million people worldwide with diabetes and the number of diabetics worldwide is expected to reach 300 million by the year 2009. Diabetic retinopathy is a leading cause of blindness and other complications of diabetes include renal disease, foot problems and neuropathic conditions.

There are two clinical forms of diabetes, each with a different pathogenesis: type 1, insulin dependent diabetes mellitus (IDDM) and type 2, non-insulin dependent diabetes mellitus (NIDDM). Of the major forms of diabetes mellitus, type 2 diabetes cases outnumber type 1 diabetes cases by a ratio of about ten to one. In type 2 diabetes, cellular resistance to the functional effectiveness of insulin results in above normal levels of insulin secretion. When this compensatory increase of insulin production cannot be maintained, and/or when cellular insulin resistance increases further, blood sugar rises, lipid and protein metabolism are disturbed, and the insidious processes of vascular complications of long-term diabetes begin.

Patients with diabetes of all types have considerable morbidity and mortality from microvascular (retinopathy, neuropathy, nephropathy) and macrovascular (heart attacks, stroke, peripheral vascular disease) pathology, all of which carry an enormous cost. For example: a) Proliferative retinopathy and/or macular edema occur in about 50% of patients with type 2 diabetes, as do peripheral and/or autonomic neuropathy. b) The incidence of diabetic renal disease is 10% to 50% depending on ethnicity. c) Diabetics have heart attacks, strokes and peripheral vascular disease at about triple the rate of non-diabetics. The cost of treating diabetes and its complications exceeds $100 billion annually. In addition to these dreadful data, insulin resistance (a prelude to type 2 diabetes in about 50% of those effected) with its associated hypertension, coagulopathy, dyslipidemia and obesity substantially adds to these morbidity, mortality and cost statistics.

In type 1 or insulin dependent diabetes mellitus (IDDM) the B cells of the pancreas, and hence the capacity to make insulin, are destroyed by what is probably an autoimmune disease. Insulin replacement is the preferred therapy.

Insulin Resistance and Type 2 Diabetes

Insulin resistance and non-insulin-dependent diabetes are prevalent in up to 35% of the population depending upon the age and nature of the subset. In the United States alone, 16 million people have type 2 diabetes and 13 million have impaired glucose tolerance. In fact type 2 diabetes has reached epidemic proportions worldwide. Because of an aging and increasingly sedentary, obese population with changing, unhealthy diets, insulin resistance is also increasing alarmingly (it is already two to three times more prevalent than type 2 diabetes). This apparent increase in the prevalence of insulin resistance and type 2 diabetes occurs in all ethnic populations, but especially in those that have migrated from their native lands to more urbanized and westernized regions of the world.

Insulin resistance is associated with several disease conditions in addition to type 2 diabetes, obesity, hypertension, and cardiovascular disease. In addition to insulin resistance, type 2 diabetes is associated with normal to elevated levels of insulin, hyperglycemia, increased levels of very low density lipoproteins (VLDL), and decreased muscle uptake of glucose. Type 2 diabetes is often associated with hypertriglyceridemia. Type 2 diabetes patients tend to develop many of the same complications associated with type 1 diabetes including nerve, eye, kidney, and coronary artery disease.

Mounting scientific evidence suggests that type 2 diabetes results from a combination of two components: 1) a hereditary, genetic component an acquired component. The genetic component of type 2 diabetes is responsible for the first stage of the disease, termed the "prediabetic" state. The prediabetic state is characterized by hyperinsulinemia and "primary" insulin resistance. Insulin responsiveness in the prediabetic state is sufficient to maintain normal glucose tolerance or at least impaired glucose tolerance.

The precise mechanism through which hyperglycemia induces insulin resistance is not understood. However, several observations have suggested that insulin resistance is due, at least in part, due to inhibition of the normal insulin receptor function. First, the hyperglycemic—type 2 diabetes state leads to reduced insulin-stimulated activities including insulin receptor autophosphorylation, insulin receptor-mediated kinase activities (including tyrosine kinase), insulin-stimulated phosphatidylinositol kinase activity, and insulin-stimulated DNA synthesis. Thus, although the receptor can bind insulin, the normal insulin-mediated transduction signals are not transmitted. The decrease in insulin receptor kinase activity has been correlated with the magnitude of the patient's hyperglycemia (Nolan et al., 1994, J. Clin. Endocrinol. Metab., 78:471-477; Maegawa et al., 1991, Diabetes, 40:815-819).

Although NIDDM is more prevalent than IDDM, its pathogenesis is not well understood. It has though been determined that NIDDM is the result of both a beta cell defect and insulin resistance. Thus, patients with type 2 diabetes have the two physiological defects of hypersecretion of insulin (during at least the early phase of type 2 diabetes) and resistance to insulin in target tissues. There is support for the belief that hyperinsulinemia is the primary defect and it is known that in the early stages of type 2 diabetes, B cell production of insulin increases. Thus, in the first phase (new onset) of NIDDM, the plasma glucose level is normal despite demonstrable insulin resistance with elevated insulin levels. In the second phase insulin resistance worsens so that postprandial hyperglycemia develops despite elevated insulin. In the third or late phase of type diabetes, insulin resistance does not change but declining insulin secretion causes fasting hyperglycemia and overt diabetes. It is possible that early phase hypersecretion of insulin causes the insulin resistance. Thus, the primary defect can be due to dysfunctional islet cells cause insulin hypersecretion which leads to insulin resistance. In support of this theory, one can note that B cell mass is intact in type 2 diabetes, while most beta cells have been destroyed in type 1 IDDM. Interestingly, the alpha cell population is increased in type 2 diabetes, resulting in an elevated ratio of alpha to beta cells and excess glucagon production.

Unfortunately, high insulin levels, such as can occur in early phase type 2 diabetes have recently been linked to an increased risk of blood clots. Thus, patients with elevated insulin also have impaired ability to dissolve blood clots (impaired fibrinolysis). Significantly, blood clot formation is a major cause of heart attack and is the cause of the most common type of stroke.

There is clearly therefore a need to treat hyperinsulinemia, such as can occur during, at least, the early phase of type 2 diabetes. Unfortunately, there are many drawbacks and deficiencies with known treatments for type 2 diabetes. Thus, current therapy for type 2 diabetes can include administration of an oral agent such as a sulfonylurea (for example acetohexamide, chlorpropamide, tolazamide, glimeripiride, glyburide or glibornuride) which acts by stimulating B cell secretion of insulin, in an attempt to overcome the insulin resistance of early phase type 2 diabetes or to address the declining insulin production by B cells in late phase, type 2 diabetes. Unfortunately, sulfonylureas increase extrapancreatic insulin receptors. Additionally, severe and prolonged hypoglycemia can follow sulfonylurea administration, which can necessitate a need for massive glucose infusions. Furthermore, oral sulfonylureas can have undesirable systemic effects. Finally, sulfonylureas typically have a duration of action of only about 12-60 hours per dose of sulfonylurea administered. Thus, a need exists for a more effective antidiabetic drug.

Anis et al. 2004 (Diabetologia, 47, 1232-1244) describes the antidiabetic effect of peptides derived from HJ loop sequence of GRK-2 and -3, members of the GRK members of the protein kinase family. Niv et al. 2004 (J. Biol. Chem., 279: 1242-1255), describes sequence-based design of c-Kit, Lyn and protein kinase B (PKB) kinase inhibitors using the canonical structure of protein kinases.

The three dimensional structure of the complex of PKA and a peptide derived from its pseudo-substrate PKI was published in 1991 (Taylor et al., Science. 1991, 253(5018), 414-20). This provides a model of the interaction of the substrate and the enzyme PKA.

Inhibitors of PKC

U.S. Pat. No. 6,686,334 discloses use of inhibitors of protein kinase C epsilon to treat pain. U.S. Pat. No. 6,811,993 describes methods for diagnosing cardiovascular and diabetes related disorders, and for identifying and evaluating treatments for cardiovascular or diabetes related disorders based on measuring PKC activity in monocytes and in vascular tissues.

U.S. Pat. No. 6,511,811 discloses methods and compositions for treatment of insulin-resistance through the inhibition of protein kinase C-mediated phosphorylation of the amino acid residue $Ser_{1270}$ of the insulin receptor and methods for testing compounds suitable for inhibition of serine-phosphorylation by protein kinase C.

U.S. Pat. No. 6,306,383 relates to the topical treatment of scars by the use of a selected protein kinase c inhibitor and an effective penetrating agent.

U.S. Pat. No. 4,923,802 relates to peptide substrates for the detection, characterization and purification of protein kinase C. A highly specific peptide substrate for protein kinase C is composed in basic form of a serine or threonine amino acid residue flanked by groups of basic amino acids composed entirely of arginine, lysine or histidine or any combination of these amino acid residues.

SUMMARY OF THE INVENTION

The present invention relates to specific inhibitors of protein kinase C(PKC) activity. Specific inhibitors, according to the present invention, may be selective to the isoenzyme epsilon of PKC, denoted herein PKC-ε while other inhibitors may be selective to any one or more isoenzyme of PKC.

The present invention provides inhibitors of protein kinase C which specifically inhibit the interaction between the enzyme and its substrate(s) and to pharmaceutical compositions comprising such compounds. The present invention further provides peptides, peptide analogs and peptidomimetics of PKC-ε derived from the PKC-ε sequence and methods for using same. The present invention further provides methods for prevention, delay, suppression and treatment of insulin resistance and type 2 diabetes, using isolated peptide analogs of PKC-ε.

According to one aspect of the present invention, insulin resistance evoked by PKC-induced serine/threonine phosphorylation of cellular proteins active in the insulin signal transduction, can be abolished or ameliorated by peptides and peptide analogs of PKC-ε which specifically inhibits the binding of PKC-ε to its substrate. According to various embodiments the molecules provided in the present invention are capable of inhibiting PKC activity or down-stream signaling.

The present invention further provides methods for identifying and synthesizing protein kinase C epsilon inhibitors and for using them for preparation of pharmaceutical compositions.

According to certain embodiments of the present invention, isolated peptides, derived from the sequence of protein kinase C epsilon (SEQ ID NO:1) as well as peptide analogs and peptidomimetics of same isolated peptides, are disclosed as having inhibitory effects on PKC activity. These inhibitory molecules may be derived from any part of the enzyme which is involved in binding to the substrate.

According to a specific embodiment the inhibitory peptides are 4-34 amino acids in length. According to another embodiment the peptides are 5-18 amino acids in length while according to yet another embodiment the peptides are 6-12 amino acids in length.

According to certain specific embodiments inhibitory peptides and analogs of the present invention are derived from the αD region of PKC-ε (SEQ ID NO:2).

According to some embodiments, the inhibitory peptide analog of PKC-ε, is a peptide having formula I:

(Formula I, SEQ ID NO: 3)
R-X-Phe-Gln-Ile-Gln-Arg-Ser-Arg-Lys-Phe-Asn-Y wherein R is a moiety capable of increasing the permeability of the peptide analog, and Y designates a terminal carboxy acid, amide or alcohol group. According to one embodiment R is a fatty acid. according to one embodiment R is myristoyl. According to one embodiment X is a direct bond or a spacer. According to another embodiment X is an amino acid. According to yet another embodiment X is a Gly residue.

According to yet another embodiment, the inhibitory peptide analog of PKC-ε, is a peptide having formula II:

(Formula II, SEQ ID NO: 4)
R-X-Asn-Leu-Met-Phe-Gln-Ile-Gln-Arg-Ser-Arg-Lys-Phe-Y wherein R is a moiety capable of increasing the permeability of the peptide analog, and Y designates a terminal carboxy acid, amide or alcohol group. According to one embodiment R is a fatty acid. According to one embodiment R is myristoyl. According to one embodiment X is a direct bond or a spacer. According to another embodiment X is an amino acid. According to yet another embodiment X is a Gly residue.

According to a specific embodiment of the present invention, the inhibitory peptide analog of PKC-ε is selected from the group consisting of:

myristoyl-Gly-Phe-Gln-Ile-Gln-Arg-Ser-Arg-Lys-Phe-Asn-amide (herein designated "peptide 12", SEQ ID NO:6);

myristoyl-Gly-Asn-Leu-Met-Phe-Gln-Ile-Gln-Arg-Ser-Arg-Lys-Phe-amide (herein designated "peptide 16", SEQ ID NO:7);

According to other embodiments of the present invention the peptides are derived from the HJ region of PKC-ε (SEQ ID NO:5).

According to yet another embodiment, the inhibitory peptide analog of PKC-ε, is a peptide having formula III:

(Formula III, SEQ ID NO: 8)
R-X-Met-Ala-(D)Lys-Gln-Pro-Pro-Phe-Y wherein R is a moiety capable of increasing the permeability of the peptide analog, and Y designates a terminal carboxy acid, amide or alcohol group. According to one embodiment R is a fatty acid. According to one embodiment R is myristoyl. According to one embodiment X is a direct bond or a spacer. According to another embodiment X is an amino acid. According to yet another embodiment X is a Gly residue.

According to a specific embodiment the inhibitory peptide or peptide analog comprises the sequence: myristoyl-Gly-Met-Ala-(D)Lys-Gln-Pro-Pro-Phe-amide (herein designated "peptide 7", SEQ ID NO:9).

According to another embodiment the inhibitory peptide or peptide analog comprises the sequence Asn-Gly-Gly-Asp-Leu-Met-Phe-Gln-Ile-Gln-Arg-Ser-Arg-Lys-Phe-Asp-Glu-Pro-Arg-Ser-Arg-Phe-Tyr-Ala-Ala-Glu-Val-Thr-Ser-Ala-Leu-Met (SEQ ID NO:2).

According to yet another embodiment the inhibitory peptide or peptide analog comprises the sequence Glu-Met-Met-Ala-Gly-Gln-Pro-Pro-Phe-Glu-Ala-Asp-Asn-Glu Asp-Asp-Leu-Phe-Glu-Ser-Ile-Leu-His-Asp-Asp-Val-Leu-Tyr-Pro-Val-Trp-Leu (SEQ ID NO:5).

According to another aspect of the present invention, any moiety known in the art to actively or passively facilitate or enhance permeability of the compound into cells may be used for conjugation with the peptide. Non-limitative examples include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides.

The cell-permeability moiety may be connected to any position in the peptide moiety, directly or through a spacer. According to specific embodiments, the cell-permeability moiety is connected to the amino or carboxy terminus of the peptide moiety. The optional connective spacer may be of varied lengths and conformations comprising any suitable chemistry including but not limited to amine, amide, carbamate, thioether, oxyether, sulfonamide bond and the like. Non-limiting examples for such spacers include amino acids, sulfone amide derivatives, amino thiol derivatives and amino alcohol derivatives.

The present invention further provides pharmaceutical compositions comprising at least one isolated peptide, peptide analog or peptidomimetic according to the invention together with a pharmaceutically acceptable excipient, diluent or carrier.

According to certain embodiments of the present invention, pharmaceutical compositions comprising an inhibitory peptide conjugate or peptide analog of PKC-ε are provided.

The pharmaceutical compositions of the present invention may be suitable for any route of administration. These pharmaceutical compositions are preferably administered by oral or nasal routes, although other routes of administration, including intravenous, intramuscular, subcutaneous, intradermal, and transdermal routes are possible and are within the scope of the present invention if they result in inhibition of PKC activity or signaling.

The present invention provides methods for modulating the activity of protein kinase C in a subject, comprising administering a therapeutically effective amount of an isolated peptide, peptide analog or peptidomimetic that is a protein kinase C inhibitor.

The present invention further provides methods for prevention, delay, suppression or treatment of disorders involving protein kinase C, including but not limited to type 2 diabetes, insulin resistance, hyperglycemia, diabetic complications and metabolic disorders.

According to specific aspect of the present invention methods for treatment of insulin resistance and type 2 diabetes by inhibition of protein kinase C epsilon are provided. Specific embodiments provide methods of treating an individual in need thereof by administering a pharmaceutical composition comprising a therapeutically effective amount of an inhibitory peptide, peptide conjugate or peptide analog of PKC-ε.

Another aspect of the present invention is directed to the use of an inhibitory peptide, peptide conjugate or peptide analog for production of a medicament useful for the treatment of diseases and disorders involving protein kinase C, including but not limited to type 2 diabetes, insulin resistance, hyperglycemia, diabetic complications and metabolic disorders.

Essentially all of the uses known or envisioned in the prior art for protein kinase C inhibitors can be accomplished with the molecules of the present invention.

By way of exemplification, the compounds disclosed in the present invention were selected for inhibition of Protein kinase C epsilon. Using the preparations and methods disclosed herein it is possible to obtain compounds that inhibit the activity of other types of protein kinase C. These and other features of the present invention will be better understood in conjunction with the figures, description, examples and claims that follow.

BRIEF DESCRIPTION OF THE DRAWINGS

The invention will better be understood in relation to the drawings and detailed description of the preferred embodiments which follow.

DETAILED DESCRIPTION OF THE INVENTION

As disclosed herein for the first time, it was shown that specific isolated peptides derived from the sequence of PKC-ε and peptide analogs of same are capable of inhibiting the activity of PKC. It was further found that these inhibitory peptides and analogs are active in vitro and in vivo in the recognized model of nutritionally induced insulin resistance and type 2 diabetes, and may serve as suitable candidates for preparation of pharmaceutical compositions for prevention, delay, suppression and treatment of insulin resistance and type 2 diabetes.

It has been shown, both in animals and humans, that several PKC isoenzymes, including PKC-α, PKC-ε and PKC-θ, are related to insulin resistance by serine phosphorylation, which is inhibitory to tyrosine phosphorylation and to insulin signaling. In the course of reducing the present invention to practice the present inventors have identified and synthesized PKC-ε inhibitory compounds, namely peptides derived from the region in PKC-ε which is involved in binding to its substrate, and tested these for inhibition of this enzyme. The inhibitory peptide analogs so identified were further tested in vitro in tissues of the Israeli Psammomys obesus (sand rat) and in vivo in the nutritionally induced diabetes in Psammomys obesus model, which is a recognized animal model for insulin resistance and type 2 diabetes.

Figure 1:
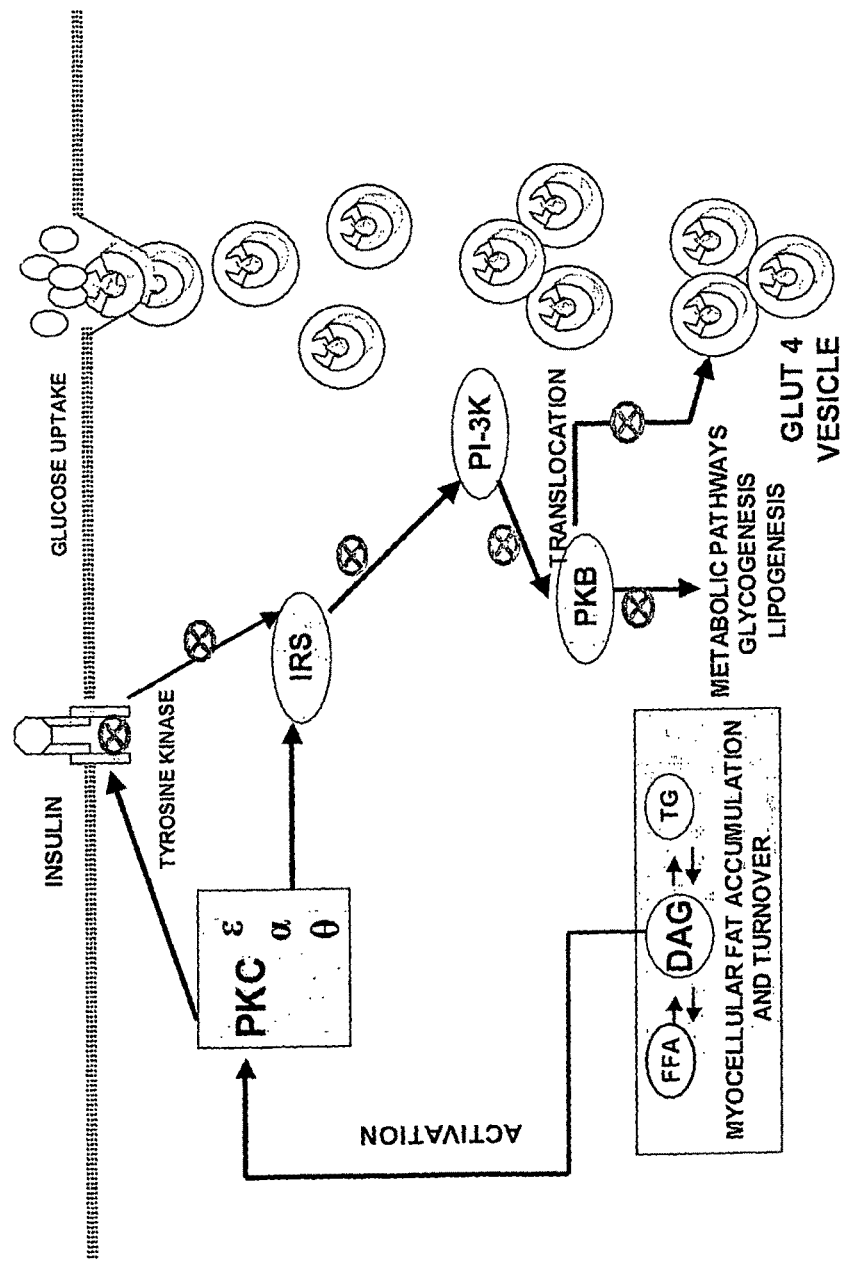
FIG. 1: A scheme summarizing the deleterious effect of PKC, which could be inhibited, with the compounds of the present invention.

As demonstrated in FIG. 1, insulin binds to the insulin receptor in the cell membrane, resulting in activation of the receptor enzyme tyrosine kinase, which phosphorylates the insulin receptor substrate (IRS). The phosphorylation occurs on the tyrosine residues of the IRS protein but it is attenuated by PKC, which phosphorylates serine residues on IRS. According to the present invention novel peptides are capable of masking the serine phosphorylation sites on IRS, preventing their phosphorylation by PKC and thus enable the continuation of insulin action. Furthermore, the phosphorylation of tyrosine residues may be regulated by the concomitant phosphorylation of serine in the normal situation. However, when PKC is overexpressed by contact with diacylglycerol (DAG), ensuing from augmented lipid accumulation in muscles (FFA or triglycerides) the serine phosphorylation prevails and the muscle cell becomes resistant to the action of insulin. This undesirable resistance may be prevented or overcome by the peptides of the present invention. The components of the insulin signaling system, dependent on the message from IRS are PI3K and protein kinase B (PKB). The latter is important for activation of pleiotropic metabolic processes, like lipogenesis and glycogen synthesis, as well as translocdation of the glucose transporter GLUT4 to the cell surface which facilitates the entry of glucose into the cell. In absence of GLUT4 translocation, the muscle glucose uptake is markedly diminished. This can be prevented or alleviated using the peptides of the present invention. Apart from phosphorylation of serine on IRS, PKC also phosphorylates serine on other components of the insulin signaling pathway, which is deleterious to insulin action and contributes to insulin resistance. These actions could be also inhibited with the compounds of the present invention.

According to the principles of the present invention the model of the interaction between the enzyme and its substrate was used to generate candidate peptides and peptide analogs corresponding to regions that are involved presumptively in the interaction of PKC and its protein substrates. Several peptides and analogs derived from regions HJ and αD of PKC-ε were designed and synthesized based on that model. The peptides were screened in vitro and in vivo for their ability to reduce the glucose levels in blood of diabetic pssamomys.

Conjugates of the peptides with hydrophobic moieties were synthesized and tested as well. According to an exemplary embodiment, a myristoyl moiety was attached to the N-terminus of the peptides in order to facilitate cell permeability of the tested molecules. The active peptides are then further tested in conjugation with different fatty acids and other moieties known in the art to enhance permeability.

The present invention is exemplified by inhibitory peptides of 4-34 amino acids, more specifically 5-18 amino acids and even more specific 6-12 amino acids.

According to certain specific embodiments inhibitory peptides and analogs of the present invention are derived from the αD region of PKC-ε (SEQ ID NO:2).

According to some embodiments, the inhibitory peptide analog of PKC-ε, is a peptide having formula I:

(Formula I, SEQ ID NO: 3)
R-X-Phe-Gln-Ile-Gln-Arg-Ser-Arg-Lys-Phe-Asn-Y wherein R is a moiety capable of increasing the permeability of the peptide analog, and Y designates a terminal carboxy acid, amide or alcohol group. According to one embodiment R is a fatty acid. According to one embodiment R is myristoyl. According to one embodiment X is a direct bond or a spacer. According to another embodiment X is an amino acid. According to yet another embodiment X is a Gly residue.

According to yet another embodiment, the inhibitory peptide analog of PKC, is a peptide having formula II:

(Formula II, SEQ ID NO: 4)
R-X-Asn-Leu-Met-Phe-Gln-Ile-Gln-Arg-Ser-Arg-Lys-Phe-Y wherein R is a moiety capable of increasing the permeability of the peptide analog, and Y designates a terminal carboxy acid, amide or alcohol group. According to one embodiment R is a fatty acid. According to one embodiment R is myristoyl.

According to one embodiment X is a direct bond or a spacer. According to another embodiment X is an amino acid. According to yet another embodiment X is a Gly residue.

According to a specific embodiment of the present invention, the inhibitory peptide analog of PKC-ε is selected from the group consisting of:

myristoyl-Gly-Phe-Gln-Ile-Gln-Arg-Ser-Arg-Lys-Phe-Asn-amide (herein designated "peptide 12", SEQ ID NO:6);

myristoyl-Gly-Asn-Leu-Met-Phe-Gln-Ile-Gln-Arg-Ser-Arg-Lys-Phe-amide (herein designated "peptide 16", SEQ ID NO:7);

According to other embodiments of the present invention the peptides are derived from the HJ region of PKC-ε (SEQ ID NO:5).

According to yet another embodiment, the inhibitory peptide analog of PKC-ε, is a peptide having formula III:

(Formula III, SEQ ID NO: 8)
R-X-Met-Ala-(D)Lys-Gln-Pro-Pro-Phe-Y wherein R is a moiety capable of increasing the permeability of the peptide analog, and Y designates a terminal carboxy acid, amide or alcohol group. According to one embodiment R is a fatty acid. According to a one embodiment R is myristoyl. According to one embodiment X is a direct bond or a spacer. According to another embodiment X is an amino acid. According to yet another embodiment X is a Gly residue.

According to a specific embodiment the inhibitory peptide analog comprises the sequence: myristoyl-Gly-Met-Ala-(D)Lys-Gln-Pro-Pro-Phe-amide (herein designated "peptide 7", SEQ ID NO:9).

TERMINOLOGY AND DEFINITIONS

The term "diabesity" relates to weight gain which does not precede insulin resistance and hyperinsulinaemia, but increased triglyceride synthesis and may occur with hyperinsulinaemia and hyperglycaemia and contribute to adipose tissue accretion.

As used herein "peptide" indicates a sequence of amino acids linked by peptide bonds. The peptide analogs of this invention comprise a sequence of 4 to 34 amino acid residues, preferably 5 to 18 residues, more preferably 6 to 12 amino acids, each residue being characterized by having an amino and a carboxy terminus.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof.

These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "analog" further indicates a molecule which has the amino acid sequence according to the invention except for one or more amino acid changes. Analogs according to the present invention may comprise also peptidomimetics. "Peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active.

Peptidomimetic compounds can have additional characteristics that enhance their therapeutic application, e.g., enhanced cell permeability, increased binding affinity and/or avidity for their respective target molecules, prolonged biological half-lives, and enhanced oral availability. The design of peptidomimetic compounds having PKC antagonist activity can be aided through computer modeling techniques well known in the art. Other methods for the design, as well as the preparation of, peptidomimetic compounds are well known in the art.

An "effective peptide" will have the activity to achieve a desired result, such as inhibition or induction of certain cell factor. Alternatively, an effective peptide will provide the cell with a beneficial or therapeutic effect, such as induction of release of a specific mediator. Thus reference to a particular peptide or analog includes the naturally occurring peptide sequence or a peptide that has the substantially the same activity as the naturally occurring sequence. "Effective peptides" of the invention also include modified peptides (with amino acid substitutions, both conservative and non-conservative) that have the same activity as a wild-type or unmodified peptide. "Salts" of the peptides of the invention contemplated by the invention are physiologically acceptable organic and inorganic salts.

As used herein and in the claims, the phrase "therapeutically effective amount" means that amount of peptide or peptide analog or composition comprising same to administer to a host to achieve the desired results for the indications disclosed herein.

As used herein and in the claims, the term "inhibitor" is interchangeably used to denote "antagonist" these terms define compositions which have the capability of decreasing certain enzyme activity or competing with the activity or function of a substrate of said enzyme.

The term "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "peptidomimetic" may be computer assisted.

The term "spacer" denotes a chemical moiety whose purpose is to link, covalently, a cell-permeability moiety and a peptide or peptidomimetic. The spacer may be used to allow distance between the cell-permeability moiety and the peptide, or it is a chemical bond of any type. Linker denotes a direct chemical bond or a spacer.

"Permeability" refers to the ability of an agent or substance to penetrate, pervade, or diffuse through a barrier, membrane, or a skin layer. A "cell permeability" or a "cell-penetration" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids and transporter peptides. Examples for lipidic moieties which may be used according to the present invention Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((-N,N,N-trimethylammoniumethyl-aminocarbonylmethylene)ethylenediamine tetraiodide; N,N"-Bis(hexadecylaminocarbonylmethylene)-N,N',N"-tris((N,N,N-trimethylammonium-ethylaminocarbonylmethyl-enediethylenetri amine hexaiodide; N,N'-Bis (dodecylaminocarbonylmethylene)-N,N"-bis((-N,N,N-trimethylammonium ethylaminocarbonylmethylene) cyclohexylene-1,4-diamine tetraiodide; 1,7,7-tetra-((-N,N,N,N-tetramethylammoniumethylamino-carbonylmethylene)-3-hexadecylaminocarbonyl-methylene-1,3,7-triaazaheptane heptaiodide; N,N,N',N'-tetra((-N,N,N-trimethylammonium-ethylaminocarbonylmethylene)-N'-(1,2-dioleoylglycero-3-phosphoethanolamino carbonylmethylene)diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl)methylamino)-octadecanoic acid; N-[12-(((7'-diethylaminocoumarin-3-yl) carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-sn-3-succinyl-glycerol; 1,3-dipalmitoyl-2-succinylglycerol, 1-hexadecyl-2-palmitoylglycero-phosphoethanolamine, and palmitoylhomocysteine.

Certain abbreviations are used herein to describe this invention and the manner of making and using it. For instance, DAG refers to diacylglycerol, DP refers to diabetes prone, DR refers to diabetes resistance, HE refers to high energy, IR refers to insulin receptor, IRS refers to insulin receptor substrate, LE refers to low energy, NIDDM refers to and is an exchangeable with the term type 2 diabetes, PKC refers to protein kinase C, TG refers to triglyceride, TK refers to tyrosine kinase, Chemistry Preferred peptides according to the present invention may be synthesized using any method known in the art, including peptidomimetic methodologies. These methods include solid phase as well as solution phase synthesis methods. The conjugation of the peptidic and permeability moieties may be performed using any methods known in the art, either by solid phase or solution phase chemistry. Some of the preferred compounds of the present invention may conveniently be prepared using solution phase synthesis methods. Other methods known in the art to prepare compounds like those of the present invention can be used and are comprised in the scope of the present invention.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Peptides:

It will be appreciated that peptides of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), *-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted by synthetic non-natural acid such as Phenylglycine, Tetrahydroisoquinoline-3-carboxylic acid (TIC), naphthylalanine, ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| phenylalanine | Phe | F |
| Proline | Pro | P |
| Serine | Ser | S |
| Threonine | Thr | T |

TABLE 1-continued

| Amino Acid | Three-Letter Abbreviation | One-letter Symbol |
|---|---|---|
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |

TABLE 2-continued

| Non-conventional amino acid | Code | Non-conventional amino acid | Code |
|---|---|---|---|
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the peptides of the present invention are preferably utilized in therapeutics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclization does not severely interfere with peptide characteristics, cyclic forms of the peptide can also be utilized.

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry. Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, some of the peptides of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224: 838-843, Gurley et al. (1986) Mol. Cell. Biol. 6:559-565 and Weissbach & Weissbach, 1988, Methods for Plant Molecular Biology, Academic Press, NY, Section VIII, pp 421-463.

If a peptide according to the present invention is a linear molecule, it is possible to place various functional groups at various points on the linear molecule which are susceptible to or suitable for chemical modification. Functional groups can be added to the termini of linear forms of the peptide. In some embodiments, the functional groups improve the activity of the peptide with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally be cleaved in vivo, either by hydrolysis or enzymatically, inside the cell. (Differ et al., J. Pharm. Sci. 57:783 (1968); Ditter et al., J. Pharm. Sci. 57:828 (1968); Differ et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (–CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include $CH_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantane, naphthalene, myristoyl, toluene, biphenyl, cinnamoyl, nitrobenzoxy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are optionally independently an aliphatic, substituted aliphatic, benzyl, substituted benzyl, aryl or a substituted aryl group. In addition, taken together with the nitrogen atom, $R_2$ and $R_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —$NH_2$, —$NHCH_3$, —$N(CH_3)_2$, —NH(ethyl), —$N(ethyl)_2$, —N(methyl) (ethyl), —NH(benzyl), —N(C1-C4 alkyl)(benzyl), —NH(phenyl), —N(C1-C4 alkyl) (phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the composition at least substantially retains its physiological activity as compared to the native peptide according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S,3S)-methyl-phenylalanine, (2S,3R)-methyl-phenylalanine, (2R, 3S)-methyl-phenylalanine and (2R,3R)-methyl-phenylalanine (Kazmierski and Hruby, Tetrahedron Lett. (1991)). Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

In the present invention any part of a peptide may optionally be chemically modified, i.e. changed by addition of functional groups. For example the side amino acid residues appearing in the native sequence may optionally be modified, although as described below alternatively other part(s) of the peptide may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

An amino acid of the peptide molecule can optionally be modified according to any one of the following exemplary types of modification (in the peptide viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a peptide according to the present invention, refers to a peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process. Furthermore, one or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Pharmacology

Apart from other considerations, the fact that the novel active ingredients of the invention are peptides, peptide analogs or peptidomimetics, dictates that the formulation be suitable for delivery of these type of compounds. In general, peptides are less suitable for oral administration due to susceptibility to digestion by gastric acids or intestinal enzymes, however it is now disclosed that the compositions according to the present invention my be preferably administered orally due to their improved permeability properties. Other routes of administration according to the present invention are intra-articular, intravenous, intramuscular, subcutaneous, intradermal, or intrathecal.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the fowl of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., Curr. Opin. Chem. Biol. 5, 447, 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, delay, alleviate or ameliorate symptoms of a disease of the subject being treated. Determination of a therapeutically effective amount is well within the capability of those skilled in the art.

Toxicity and therapeutic efficacy of the fragments and analogs described herein can be determined by standard pharmaceutical procedures in cell cultures or experimental animals, e.g., by determining the 1050 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

In one particularly preferred embodiment according to the present invention, the peptides are administered orally (e.g. as a syrup, capsule, or tablet).

In certain embodiments, peptide delivery can be enhanced by the use of protective excipients. This is typically accomplished either by complexing the peptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy, 1998, Biotechnol. Prog. 14, 108; Johnson et al., 1996, Nature Med. 2, 795; Herbert et al., 1998, Pharmaceut. Res. 15, 357) a dry powder composed of biodegradable polymeric microspheres containing the protein in a polymer matrix that can be compounded as a dry formulation with or without other agents.

The foregoing formulations and administration methods are intended to be illustrative and not limiting. It will be appreciated that, using the teaching provided herein, other suitable formulations and modes of administration can be readily devised. Formulations of the present invention suitable for oral administration may be presented as discrete units such as capsules, cachets, tablets, lozenges comprising the peptide(s) in a flavored base, usually sucrose and acacia and tragacanth; pastilles comprising the active ingredient(s) in an inert base such as gelatin and glycerin, or sucrose and acacia; and mouth washes comprising the active ingredient(s) in a suitable liquid carrier. Each formulation generally contains a predetermined amount of the active peptide(s); as a powder or granules; or a solution or suspension in an aqueous or non-aqueous liquid such as a syrup, an elixir, an emulsion or draught and the like.

A tablet may be made by compression or moulding, optionally with one or more accessory ingredients. Compressed tablets may be prepared by compressing in a suitable machine the active peptide(s) in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Moulded tablets may be made by moulding in a suitable machine a mixture of the powdered peptide(s) moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

A syrup may be made by adding the active peptide(s) to a concentrated, aqueous solution of a sugar, for example, sucrose, to which may also be added any necessary ingredients. Such accessory ingredients) may include flavorings, an agent to retard crystallization of the sugar or an agent to increase the solubility of any other ingredients, such as a polyhydric alcohol, for example, glycerol or sorbitol.

In addition to the aforementioned ingredients, the formulations of this invention may further include one or more accessory ingredient(s) selected from diluents, buffers, flavoring agents, binders, surface active agents, thickeners, lubricants, preservatives, (including antioxidants) and the like.

It will be understood that the dosage may be an escalating dosage so that low dosage may be administered first, and subsequently higher dosages may be administered until an appropriate response is achieved. Also, the dosage of the composition can be administered to the subject in multiple administrations in the course of the treatment period in which a portion of the dosage is administered at each administration.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Materials and Methods

For assaying the insulin signaling pathway components and electronmicroscopic examination of the pancreatic beta cells, animals were killed by decapitation in the fed state in the morning three days after the third intraperitoneal peptide injection. Blood was collected and serum insulin levels was determined by radioimmunoassay, using anti-human antibodies. The gastrocnemius muscles from both legs were excised, immediately frozen in liquid nitrogen, and then stored at $-80°$ C.

Immunoblot analysis of insulin signaling molecules were performed using muscle homogenates prepared in a homogenization buffer that contained 20 mmol/l HEPES, 8 mmol/l EDTA, 0.2 mmol/l $Na_3VO_4$, 10 mmol/l $Na_4P_2O_7$, 2.5 mmol/l, 2 mM phenylmathylsulfonyl fluorid, 160 mmol/l NaF, 2 mmol/l DCA, 1% Triton X-100, 1% protease inhibitor cocktail and 1% phaphatase inhibitor cocktail (Sigma®) pH 7.4. Equal amount of cell lysate were dissolved in Laemmli buffer and subjected to SDS-PAGE gel separation. The separated proteins were transferred to nitrocellulose membranes. Immunoreactive proteins were made visible using horseradish-peroxidase-coupled secondary antibodies and enhanced chemiluminescence reagents. All protein data were quantified by densitometry.

Rabbit polyclonal antibodies against IRS-1, IRS-1 phosphorylated at ser 636,639, PKB-AKT, PKB-AKT phosphorylated at ser473 were obtained from Cell Signaling Technology Inc. Rabbit polyclonal antibody against GLUT4 was obtained from Chemicon(USA) and mouse monoclonal antibody against actin was obtain from MP Biomedicals Inc.

The electronmicroscopic examination of pancreatic beta cells was performed on slices of pancreatic paraffin blocks according to the method of Joins et al., 2002, Virchovs Arch 440: 63-69.

Example 1

Nutritionally Induced Diabetes in Psammomys Obesus Model

Background

Psammomys is a very appropriate model for the study of effects of antidiabetic modalities especially since it does not exhibit any inborn diabetic mutation except being prone to hyperglycemia and type 2 diabetes, when placed on an affluent nutrition regimen.

The main native nutrient of the desert gerbil Psammomys obesus (often nicknamed sand rat) is a halophilic plant, Atriplex halimus, (saltbush). Psammomys never exhibits diabetes in its native habitat but develops hyperglycemia, hyperinsulinemia and overt type 2 diabetes when transferred from the desert shores of the Dead Sea to standard laboratory diet, regarded as high energy (HE) diet. Maintaining the animals on a specially devised low energy (LE) diet, prevents the hyperglycaemia and enabled the establishment of a stable, reproducible colony. The animals are not hyperphagic but when offered the HE diet gradually lapse from normalcy (stage A) into pronounced insulin resistance, evident by hyperinsulinaemia (stage B), hyperinsulinaemia with hyperglycaemia (stage C), and finally into hypersecretion-induced insulin deficiency due to beta-cell apoptosis and necrosis (stage D). The course of diabetes progress in Israeli Psammomys was described in detail in several publications of Ziv E. and Shafrir E. It should be emphasized that weight gain does not precede insulin resistance and hyperinsulinaemia, but increased triglyceride (TG) synthesis may occur with hyperinsulinaemia and hyperglycaemia and may contribute to adipose tissue accretion, a condition which is herein termed "diabesity". TG deposition in adipose and nonadipose tissues, primarily muscles is driven by hepatic lipogenesis, which continues unabated despite insulin resistance, since the liver rather than adipose tissue is the main site of lipogenesis. It is remarkable that the progress of Psammomys to diabesity may be reversed by food restriction for just a few days, before apoptosis and β-cell degranulation set in.

Among the several PKC isoenzymes probed with specific antibodies PKC-ε was most significantly overexpressed in the skeletal muscle of Psammomys, in the hyperglycaemic-hyperinsulinaemic stage C compared with the nondiabetic stage A. About ⅓ of total PKC-ε cell content was translocated from the cytosol into the membrane fraction, which indicates not only overexpression but increased activity as well. The membranal PKC-α and β were also elevated but to a lower extent. The expression of several PKC isoenzymes in diabetes resistant (DR) and diabetes prone (DP) Psammomys lines were compared. The DR line was isolated from the parent Psammomys colony by assortative mating of individuals, which did not exhibit hyperglycaemia and hyperinsulinaemia on high energy (HE) diet. Interestingly, a significant overexpression of PKC-ε was also observed in the normoglycaemic stage A of DP Psammomys compared with the DR line, which indicates that PKC-ε overexpression precedes the onset of overt insulin resistance. Thus, PKC-ε overexpression in stage A may be considered as a marker of "prediabetic" or "preinsulinemic" stage and of propensity of a given individual to progress to overt diabetes on HE diet. It is, however, without untoward consequences on low energy diet.

Since PKC-ε overexpression resulted in impaired tyrosine kinase (TK) activation by insulin and reduced GLUT4, which indicates an impaired PI3K activation, further negative downstream defect in insulin signaling were investigated. The activity of PKB/Akt, an enzyme responsible for the activation of pleiotropic metabolic systems within the cell, was determined in human embryonic kidney cells (HEK 293) transfected with insulin receptor (IR) and PKC-ε plasmids. Stimulation with phorbol ester (TPA) clearly showed that the activation of PKC-ε was coupled with a significant reduction of PKB expression and inhibition of PKB activity. These results indicate that PKC-ε inhibits PKB activation subsequent to inhibition of insulin receptor substrate (IRS) phosphorylation by TK and has a far-reaching negative effect on metabolic reactions dependent on insulin signaling.

Experimental

Figure 2:
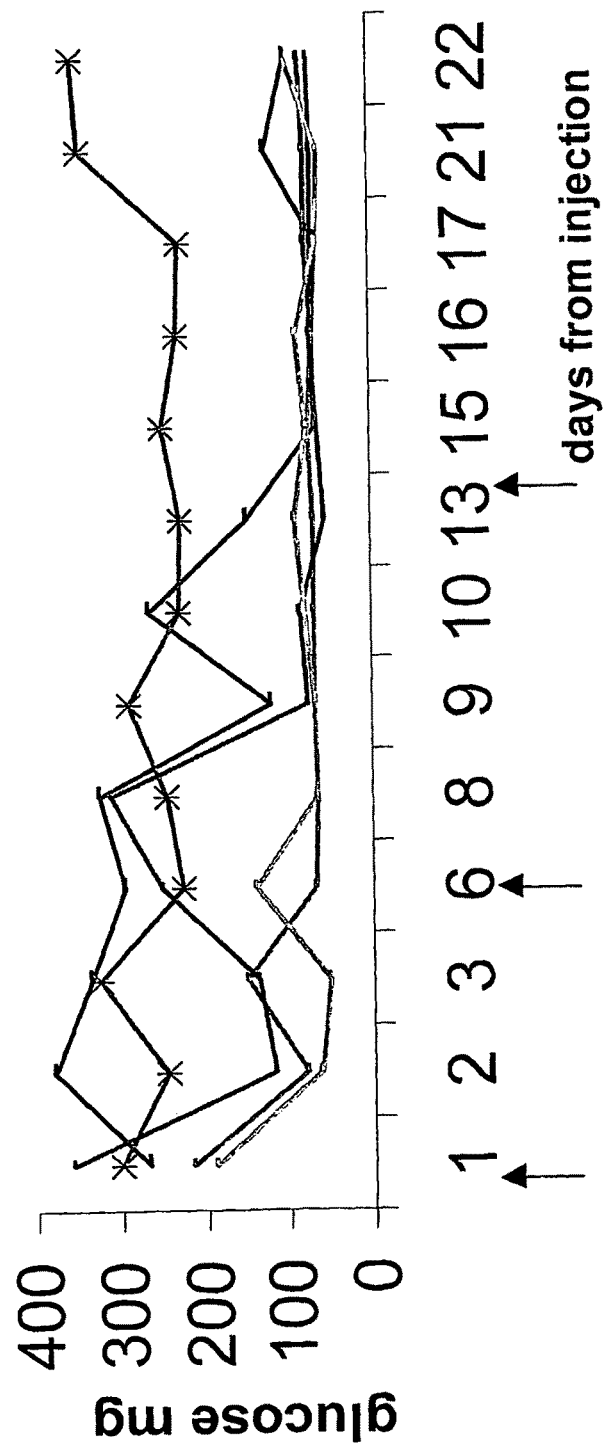
FIG. 2: Illustrates the hypoglycemic effect (in glucose mg/dl) of three injections, marked by arrows, of peptide 12 (SEQ ID NO:6). The line with asterisk represents the control animal. Other lines are those of individual injected animals.
Figure 3:
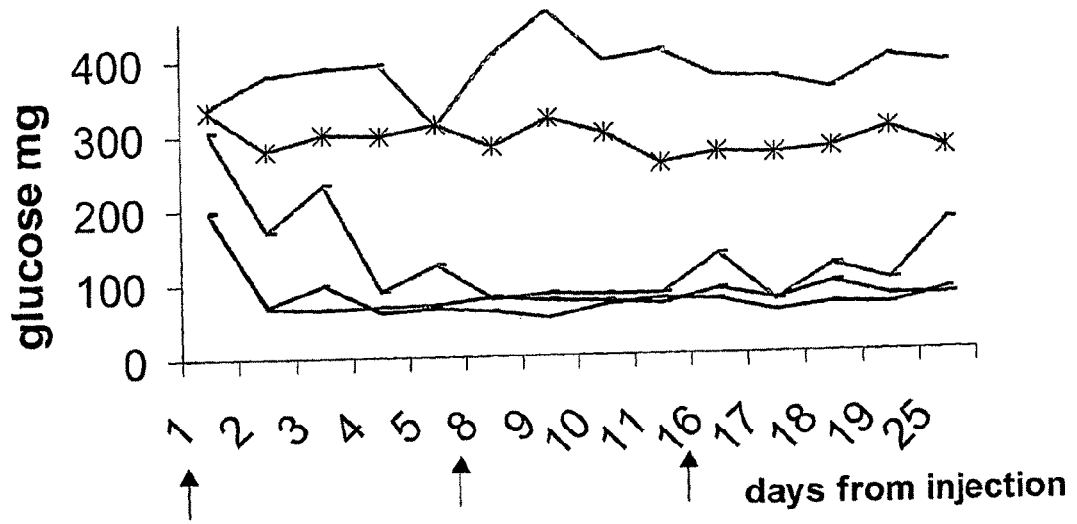
FIG. 3: Describes the hypoglycemic effect (in glucose mg/dl) of three injections, marked by arrows, of peptide 16 (SEQ ID NO:7). The line with asterisk represents the control animal. Other lines are those of individual injected animals.
Figure 4:
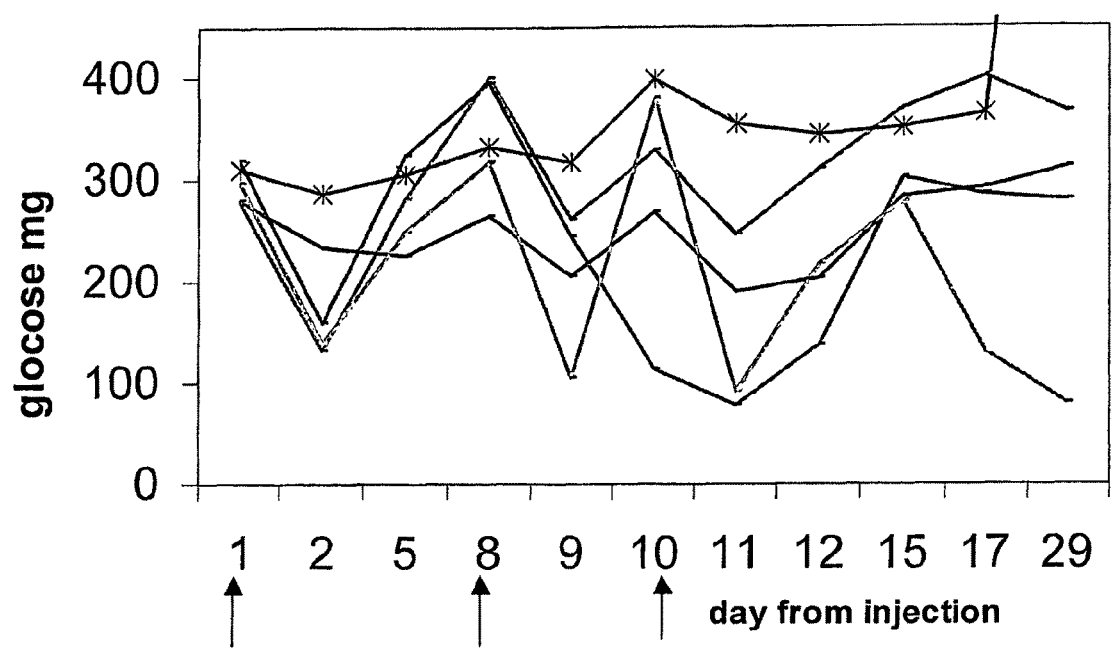
FIG. 4: Depicts the hypoglycemic effect (in glucose mg/dl) of three injections, marked by arrows, of peptide 7 (SEQ ID NO:9). The line with asterisk represents the control animal. Other lines are those of individual injected animals.

Psammomys obesus gerbils males or females weighing 160-200 g in the fed state were used. The animals were placed first for about 2 weeks on a "high energy diet" to render them hyperglycemic and hyperinsulinemic, which actually represents nutritionally induced type 2 diabetes. The animals were then injected intraperitoneally with 10 mg/kg of the peptide dissolved in dimethylsulphoxide solvent (or with solvent alone in controls). No meaningful changes were observed in the animals eating pattern or weight during the treatment period. Whole blood glucose was measured by a glucometer on a minidroplet of blood withdrawn from the end of the tail. Three injections were given 5 days apart and after 14 days or earlier the high blood glucose levels of the animals became normal, the controls remained at the 300-400 mg/dl level. The normal level lasted at least for 3 to 5 days after the last injection. FIGS. 2-4 show the hypoglycemic effect of three injections of the reactive peptides, marked by red arrows. The line with asterisk represents the control animal. Other lines are those of individual injected animals.

In some animals serum insulin level was also measured, in blood drawn from the heart (or at sacrifice). The insulin levels were markedly reduced but not completely normal.

Lower and higher doses of peptides are then tested as well as the duration of the effect after the last injection on the high-energy diet. The preventive effect, analyzed by injecting the animals with the peptide first, then placing them on the high-energy diet and measuring whether the rise in glucose was prevented, is also tested.

Example 2

Immunostaining of Beta Cells

Figure 5A:
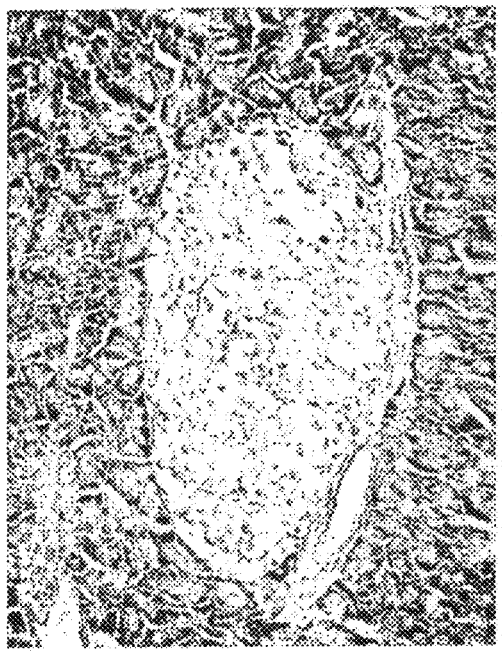
FIG. 5A: Represents hematoxylin-eosin stained beta cells in diabetic (left) and treated (right) Psammomys.
Figure 5A:
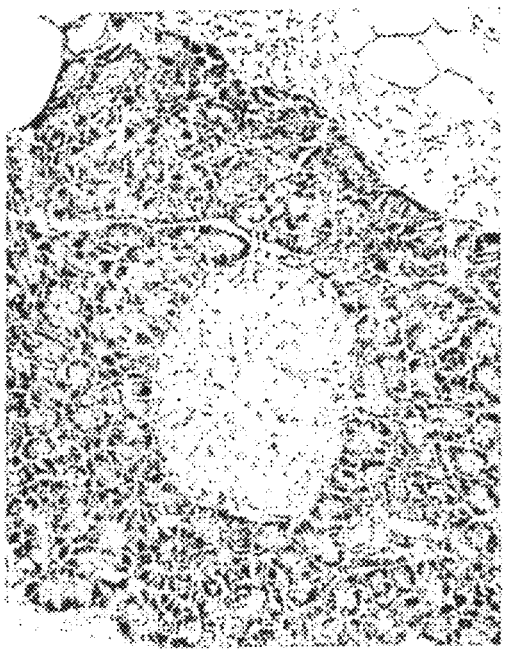
Figure 5B:
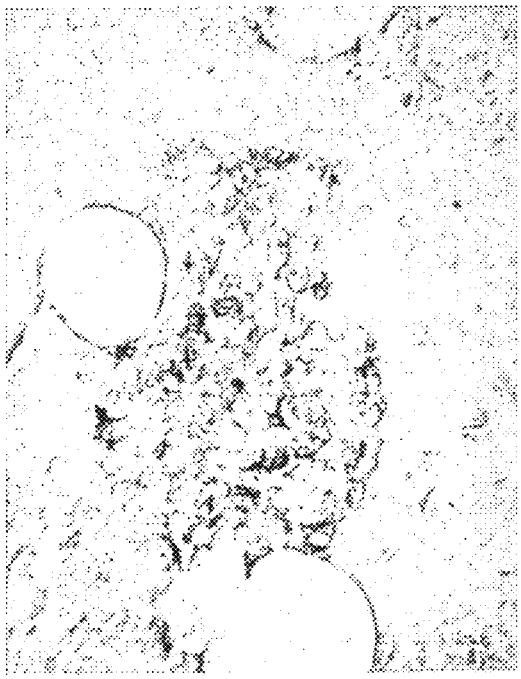
FIG. 5B: Represents insulin immunostained beta cells in diabetic (left) and treated (right) Psammomys.
Figure 5B:
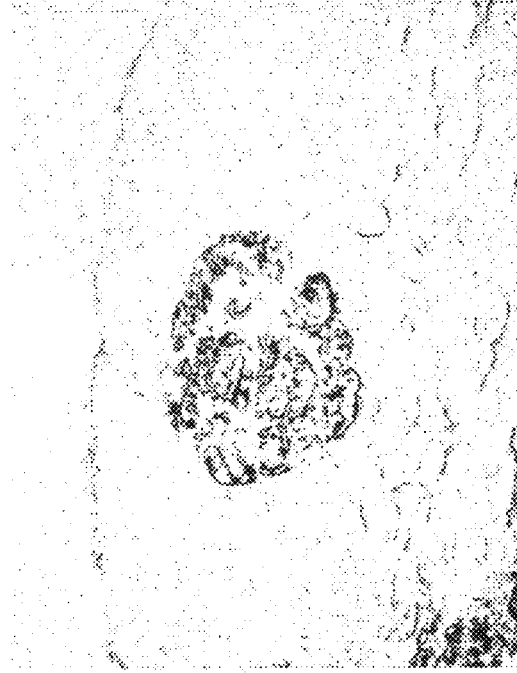

The histologic and immunostaining properties of the pancreatic beta cells in diabetic Psammomys gerbils injected with peptide 12 were investigated in order to check whether the beta cells are protected from hyperglycemia. In diabetic animals there is a considerable deterioration of the beta cell structure following the nutritionally induced diabetes and a marked depletion of the insulin content due to insulin oversecretion to compensate for the hyperglycemia. It was found that the peptide treatment for 14 days markedly improved the beta cell structure and replenished the immunostainable insulin content of the pancreatic beta cells. FIGS. 5A and 5B describe representative hematoxylin-eosin stained beta cell and insulin immunostained beta cells in diabetic and treated animals. Additional experiments are performed to demonstrate that administration of the peptides prior to the high energy diet prevents the onset of diabetes and hyperglycemia and does not produce any lesion to beta cells.

Example 3

Phosphorylation of Signal Proteins

Figure 6:
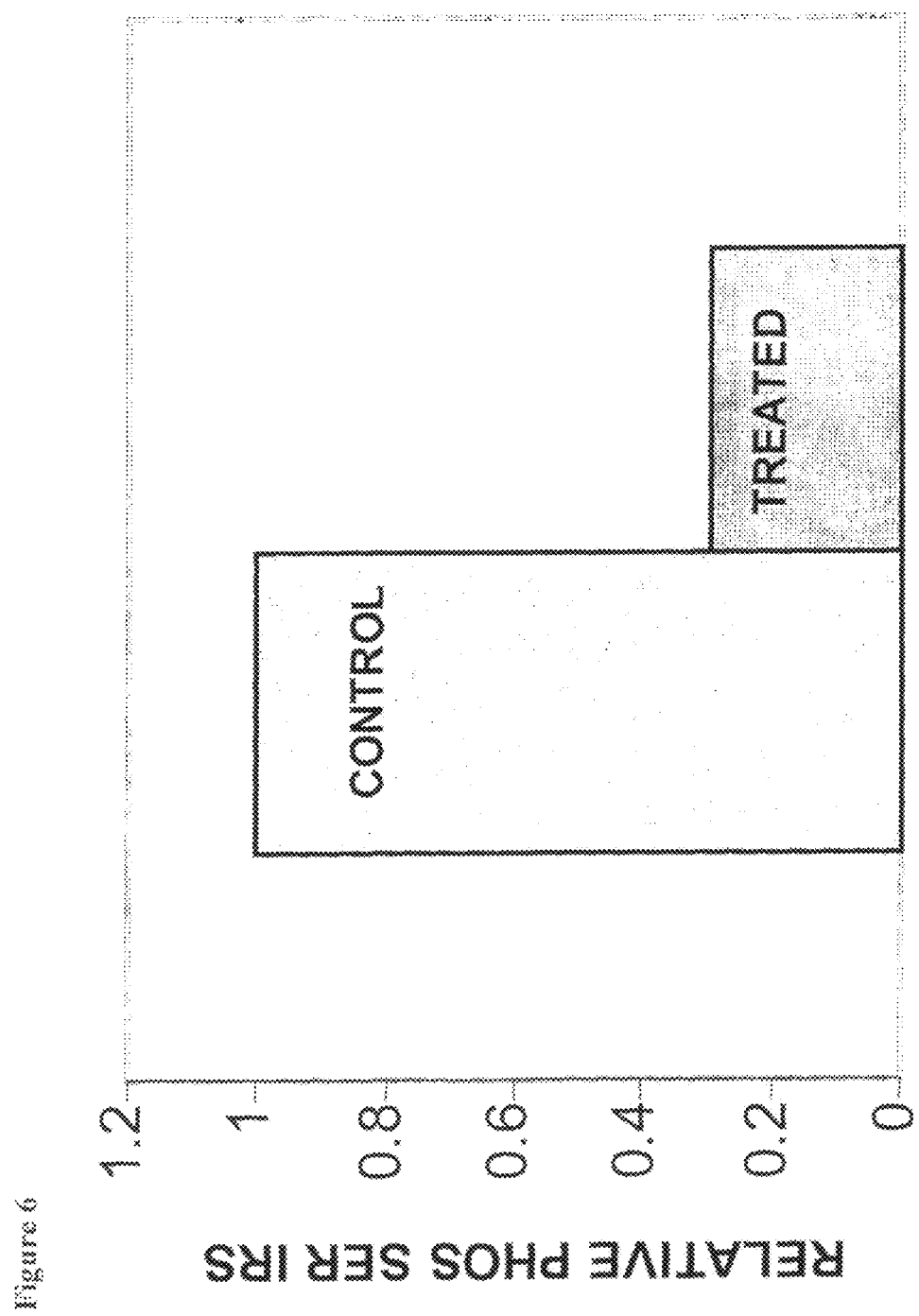
FIG. 6: Represents the relative extent of serine phosphorylation of IRS by PKC as determined by immunoblot with a specific antibody.
Figure 7:
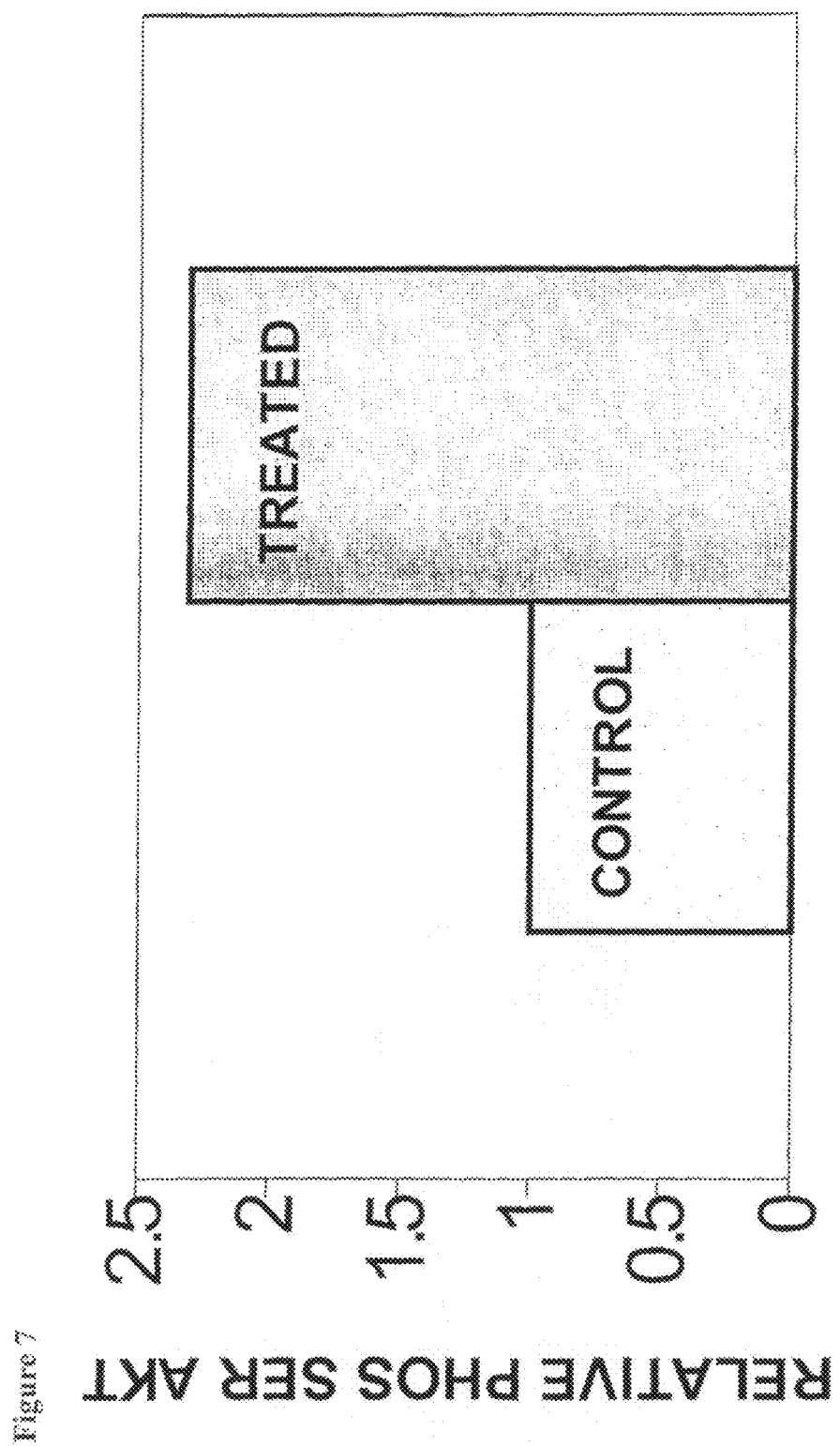
FIG. 7: shows the relative extent of phosphorylation of serine in PKB-AKT.
Figure 8:
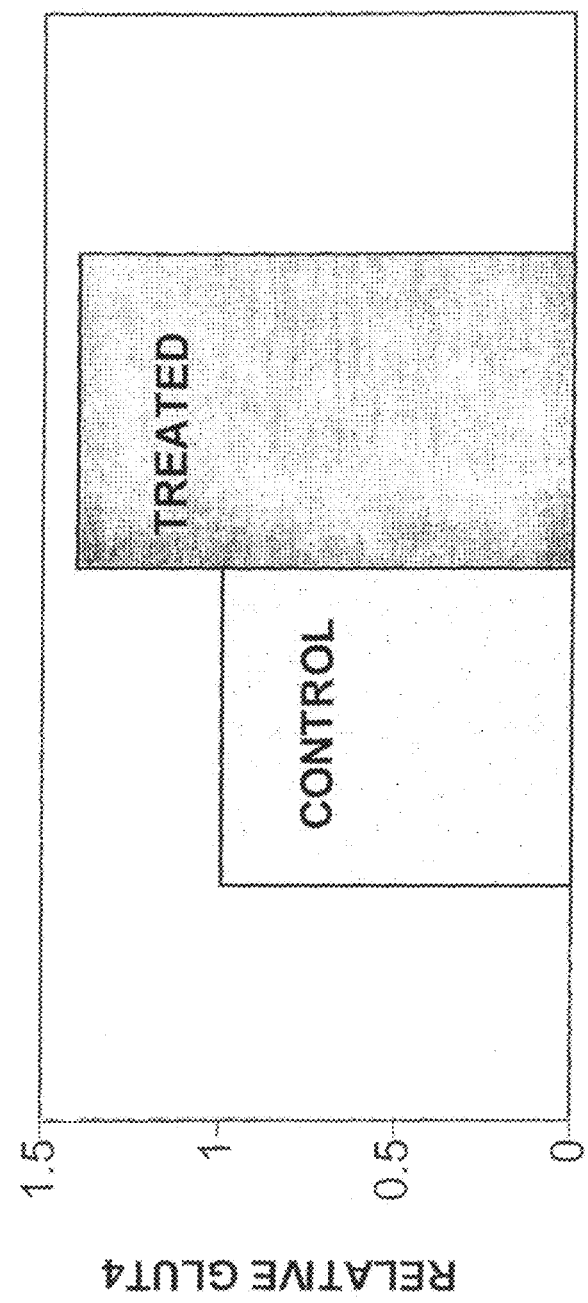
FIG. 8: Demonstrates the relative amount of the glucose transporter GLUT4 protein following the treatment with peptide 12.

The extent of phosphorylation of the components of the insulin signaling pathway (signal proteins) in the muscle lysates of the treated and non-treated animals " " was investigated. FIG. 6 presents the relative extent of serine phosphorylation of IRS by PKC as determined by immunobloting with a specific antibody. In the treated animal the extent of serine phosphorylation is much lower, attesting to the prevention of serine phosphorylation by peptide 12. FIG. 7 shows the relative extent of phosphorylation of serine in PKB/AKT. As shown in the figure, serine phosphorylation was reduced in the treated animal indicating a proper activation of the IRS receptor following tyrosine phosphorylation. The PKB/Akt, in contrast to other components of the insulin signaling which are activated by tyrosine phosphorylation, is activated by serine phosphorylation. FIG. 8 shows the relative amount of the glucose transporter GLUT4 protein which was elevated following the treatment with peptide 12. This observation is very important, demonstrating the effect of peptide 12 on increasing muscle glucose uptake and reducing the insulin resistance.

These experiments also demonstrate that the injected peptide entered the muscle cells in which it exerted its marked serine masking action.

Example 5

Prior Administration of Peptides

The prevention of diabetes induced by high energy diet by prior administration of the peptides of the invention is tested. Animals receive a dose or doses of the peptide and then transferred from low energy to high energy diet. The onset of insulin resistance and diabetes usually takes about two weeks and it is sometimes needed to supplement the animals with additional dose of peptide to keep them in normal, nondiabetic condition, as compared to non-treated controls which are lapse into diabetes. Blood levels of glucose and insulin are followed and tissue samples taken for investigation of any changes in the previously described parameters which may differ from normal.

The invention claimed is:

1. An isolated peptide comprising the amino acid sequence selected from the group consisting of SEQ ID NO:6 and SEQ ID NO:7.

2. The peptide of claim 1 wherein the peptide is conjugated to a moiety capable of facilitating penetration into a cell.

3. The peptide of claim 1 comprising the amino acid sequence myristoyl-Gly-Phe-Gln-Ile-Gln-Arg-Ser-Arg-Lys-Phe-Asn-amide (SEQ ID NO:6).

4. The peptide of claim 1 comprising the amino acid sequence myristoyl-Gly-Asn-Leu-Met-Phe-Gln-Ile-Gln-Arg-Ser-Arg-Lys-Phe-amide (SEQ ID NO:7).

5. A pharmaceutical composition comprising an isolated peptide according to claim 1, and a pharmaceutically acceptable excipient, diluent or carrier.

* * * * *

UNITED STATES PATENT AND TRADEMARK OFFICE
CERTIFICATE OF CORRECTION

PATENT NO. : 8,575,307 B2  Page 1 of 1
APPLICATION NO. : 11/993691
DATED : November 5, 2013
INVENTOR(S) : Shafrir et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1605 days.

Signed and Sealed this
Twenty-second Day of September, 2015

Michelle K. Lee
*Director of the United States Patent and Trademark Office*